United States Patent
Mathan

(10) Patent No.: US 8,059,136 B2
(45) Date of Patent: Nov. 15, 2011

(54) HIERARCHICHAL RAPID SERIAL VISUAL PRESENTATION FOR ROBUST TARGET IDENTIFICATION

(75) Inventor: Santosh Mathan, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 1007 days.

(21) Appl. No.: 11/954,151

(22) Filed: Dec. 11, 2007

(65) Prior Publication Data
US 2009/0150821 A1    Jun. 11, 2009

(51) Int. Cl.
G09G 5/00    (2006.01)

(52) U.S. Cl. ........ 345/619; 345/581; 345/625; 382/224; 382/225

(58) Field of Classification Search .................. None
See application file for complete search history.

(56) References Cited

U.S. PATENT DOCUMENTS

| | | | |
|---|---|---|---|
| 4,175,860 A | 11/1979 | Bacus | |
| 4,777,525 A | 10/1988 | Preston, Jr. | |
| 5,642,431 A | 6/1997 | Poggio et al. | |
| 6,148,096 A | 11/2000 | Pressman et al. | |
| 6,181,818 B1 | 1/2001 | Sato et al. | |
| 6,246,785 B1 | 6/2001 | Molnar et al. | |
| 6,418,430 B1 | 7/2002 | DeFazio et al. | |
| 6,925,613 B2 | 8/2005 | Gibson | |
| 7,110,586 B2 | 9/2006 | Bacus et al. | |
| 7,194,114 B2 | 3/2007 | Schneiderman | |
| 7,212,660 B2 | 5/2007 | Wetzel et | |
| 7,835,581 B2 * | 11/2010 | Mathan et al. | 382/224 |
| 2004/0119684 A1 | 6/2004 | Back et al. | |
| 2005/0084136 A1 * | 4/2005 | Xie et al. | 382/107 |
| 2005/0175243 A1 * | 8/2005 | Luo et al. | 382/224 |
| 2007/0061720 A1 | 3/2007 | Kriger | |
| 2007/0173699 A1 | 7/2007 | Mathan et al. | |
| 2008/0069480 A1 * | 3/2008 | Aarabi et al. | 382/305 |
| 2008/0259022 A1 * | 10/2008 | Mansfield et al. | 345/156 |

OTHER PUBLICATIONS

Title: Spatial Signatures of Visual Object Recognition Events Learned from Single-trial Analysis of EEG, Author: Sajda et al., pp. 2087-2090, Publication: IEEE, Date: Sep. 17-21, 2003.*

* cited by examiner

*Primary Examiner* — Kee M Tung
*Assistant Examiner* — Jwalant Amin
(74) *Attorney, Agent, or Firm* — Ingrassia Fisher & Lorenz, P.C.

(57) ABSTRACT

A system and method of efficiently and effectively triaging an image that may include one or more target entities are provided. An image that may include one or more target entities is retrieved. The retrieved image is then divided into a plurality of sub-images, and each sub-image is displayed in a display region to a user. Each sub-image that was previously displayed is then divided into a plurality of sub-images, and each sub-image that was just divided is displayed to the user in the display region. The steps in the previous sentence are then repeated a determined number of times. During the initial display of the sub-images, and during each subsequent recursion, data are collected from the user and estimates of target entity locations are derived from the collected data.

10 Claims, 4 Drawing Sheets

HIERARCHICHAL RAPID SERIAL VISUAL PRESENTATION FOR ROBUST TARGET IDENTIFICATION

STATEMENT REGARDING FEDERALLY SPONSORED RESEARCH OR DEVELOPMENT

This invention was made with Government support under contract HM1582-05-C-0046 awarded by the Defense Advanced Research Projects Agency (DARPA). The Government has certain rights in this invention.

TECHNICAL FIELD

The present invention generally relates to a system and method for efficiently conducting rapid serial visual presentation (RSVP) image triage and, more particularly, to a system and method for conducting more robust RSVP image triage.

BACKGROUND

Analysts in various professions may, at times, be called upon to search relatively large collections of imagery to identify, if present, various types of relevant information (referred to herein as "a target entity" or "target entities") in the collection of imagery. For example, medical analysts sometimes diagnose a physical impairment by searching complex imagery collections to identify one or more target entities therein that may be the cause of the physical impairment. Moreover, intelligence analysts may be called upon to search relatively complex imagery collections to identify target entities therein that may relate to various types of intelligence gathering activities.

Advancements in both image collection and storage technology presently allow for the relatively low-cost storage of large volumes of high-quality imagery. However, the cost of searching through large sets of imagery for target entities can often be substantial. Indeed, in many professions, such as intelligence gathering, effective searching may rely on the expertise of highly skilled analysts, who typically search through relatively large sequences of images in a relatively slow manner. Presently, the number of skilled analysts available to search the amount of imagery that is stored, or can potentially be stored, is in many instances insufficient.

In response to the foregoing, there has relatively recently been a focus on developing various systems and methods for triaging imagery. One of the methods that has shown promise combines electroencephalography (EEG) technology and rapid serial visualization presentation (RSVP). Various implementations of this combination have been researched and developed. For example, various researchers have experimented with a system in which users are presented, using the RSVP paradigm, a sequence of images, some of which may include particular types of target entities. During the RSVP presentation, EEG data are collected from the users. The collected EEG data are used to assign probabilities to each image. The probabilities are representative of the likelihood that an image includes a target.

Although useful in sorting a sequence of images, the above described system and method, as well as other systems and methods that employ these same technologies, do suffer certain drawbacks. For example, present systems and methods assume that the presence of a target is uniformly likely over the entirety of an image. As a consequence, areas that are less likely to include targets may be given the same weight as areas that are more likely. Additionally because each area of an image is typically viewed only once, common events, such as eye blinks, or a turn of the head, or various other momentary lapses, can increase the likelihood of missing one or more targets.

Hence, there is a need for a RSVP presentation technique that is robust to momentary lapses. There is also a need for approaches that allow a user to exploit contextual cues. The present invention addresses one or more of these needs.

BRIEF SUMMARY

In one embodiment, and by way of example only, a method of conducting image triage of an image that may include one or more target entities includes retrieving an image, dividing the retrieved image into a plurality of sub-images, and displaying each sub-image in a display region to a user. Each sub-image that was just displayed is then divided into a plurality of sub-images, and each sub-image that was just divided is displayed to the user in the display region. The steps in the previous sentence are then repeated a determined number of times.

In yet another exemplary embodiment, a system for conducting image triage of an image that may include one or more target entities includes a display device and a processor. The display device is operable to receive display commands and, in response thereto, to display an image in a display region. The processor is coupled to the display device and is configured to selectively retrieve an image, divide the image into a plurality of sub-images, and command the display device to display each sub-image to a user in the display region. The processor is further configured to divide each sub-image that was just displayed into a plurality of sub-images, command the display device to display each sub-image that was just divided to the user in the display region, and repeat these steps a determined number of times.

Furthermore, other desirable features and characteristics of the image triage system and method will become apparent from the subsequent detailed description and the appended claims, taken in conjunction with the accompanying drawings and this background.

BRIEF DESCRIPTION OF THE DRAWINGS

The present invention will hereinafter be described in conjunction with the following drawing figures, wherein like numerals denote like elements, and wherein.

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background or the following detailed description.

Figure 1:
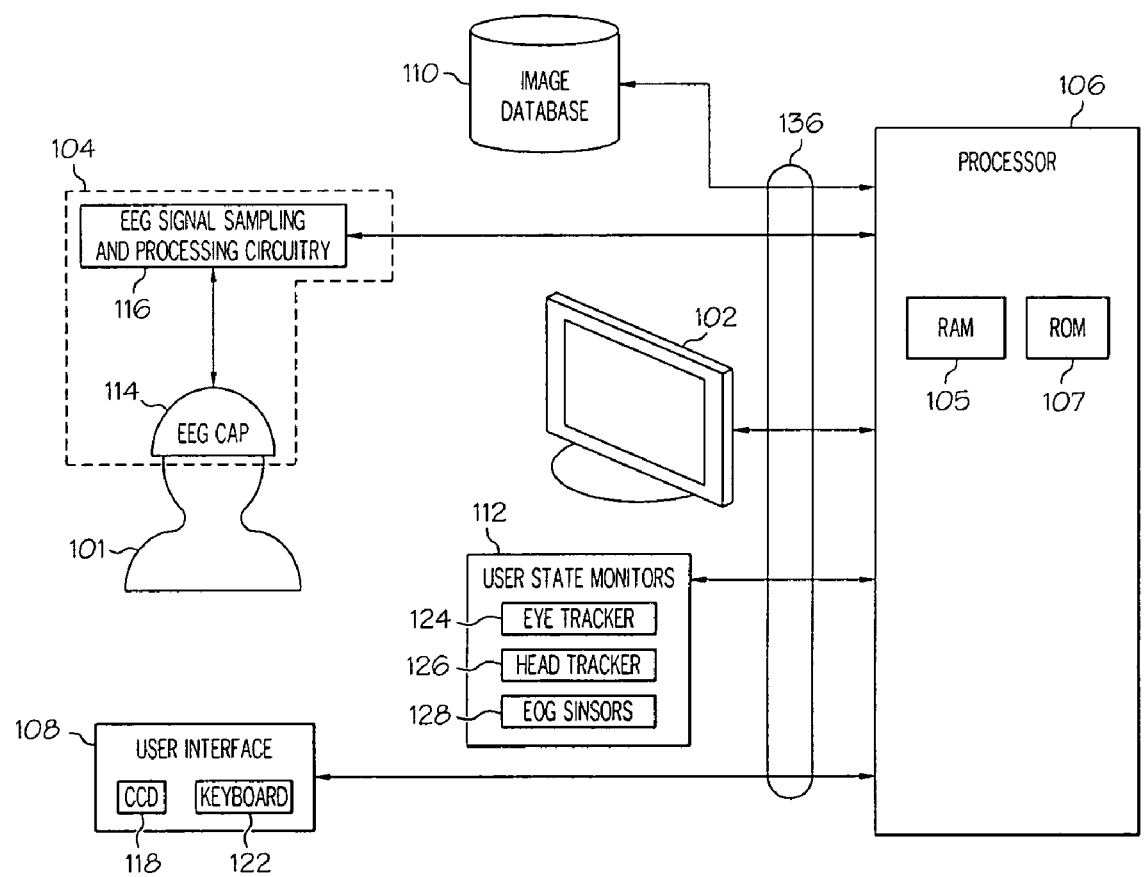
FIG. 1 depicts a functional block diagram of an exemplary image triaging system.

Turning first to FIG. 1, a functional block diagram of an exemplary system 100 that may be used to triage images is depicted. The depicted system 100 includes a display device 102, a data collector 104, and a processor 106. As FIG. 1 further depicts, in some embodiments the system 100 may additionally include a user interface 108, an image database 110, and one or more user state monitors 112. The display device 102 is in operable communication with the processor 106 and, in response to display commands received therefrom, displays one or more images to a user 101. It will be appreciated that the display device 102 may be any one of numerous known displays suitable for rendering graphic, icon, and/or textual images in a format viewable by the user 101. Non-limiting examples of such displays include various cathode ray tube (CRT) displays, and various flat panel displays such as, for example, various types of LCD (liquid crystal display) and TFT (thin film transistor) displays. The display may additionally be based on a panel mounted display, a head up display (HUD) projection, or any known technology.

The data collector 104 in the depicted embodiment is a neurophysiological data collector that is configured to be disposed on, or otherwise coupled to, the user 101, and is operable to selectively collect neurophysiological data from the user 101. Preferably, and as depicted in FIG. 1, the neurological data collector 104 is implemented as an electroencephalogram (EEG) system, and most preferably as a multi-channel EEG cap 114, and appropriate EEG signal sampling and processing circuitry 116. It will be appreciated that the number of EEG channels may vary. Moreover, the EEG signal sampling and processing circuitry 116 may be implemented using any one of numerous known suitable circuits and devices including, for example, one or more analog-to-digital converters (ADC), one or more amplifiers, and one or more filters. No matter the particular number of EEG channels and the particular type of EEG signal sampling and processing circuitry 116 that is used, it is in operable communication with, and is configured to supply the collected EEG data to, the processor 106. As will be described in more detail further below, the EEG signal sampling and processing circuitry 116 is further configured to receive trigger signals from the processor 106, and to record the receipt of these trigger signals concurrently with the EEG signals.

The user interface 108 is in operable communication with the processor 106 and is configured to receive input from the user 101 and, in response to the user input, supply various user interface signals to the processor 106. The user interface 108 may be any one, or combination, of various known user interface devices including, but not limited to, a cursor control device (CCD), such as a mouse, a trackball, or joystick, and/or a keyboard, one or more buttons, switches, or knobs. In the depicted embodiment, the user interface 102 includes a CCD 118 and a keyboard 122. The user 101 may use the CCD 118 to, among other things, move a cursor symbol on the display device 102 and select regions of an image displayed on the display device 102, and may use the keyboard 122 to, among other things, input various data. As will be described further below, the user 101 may additionally use either the CCD 118 or keyboard 122 to selectively supply physical response data, the purpose of which are also described further below.

The one or more user state monitors 112, if included, are operable to selectively collect various data associated with the user 101. The one or more user state monitors 112 may include at least an eye tracker 124, a head tracker 126, and one or more EOG (electrooculogram) sensors 128. The eye tracker 124, if included, is configured to detect the movement of one or both of the user's pupils. The head tracker 126, if included, is configured to detect the movement and/or orientation of the user's head. The EOG sensors 128, if included, are used to detect eye blinks and various eye movements of the user 101. Although any one of numerous devices may be used to implement the eye tracker 124 and head tracker 126, in the depicted embodiment one or more appropriately mounted and located video devices, in conjunction with appropriate processing software components are used to implement these functions. Though not explicitly depicted in FIG. 1, appropriate signal sampling and processing circuitry, if needed or desired, may be coupled between the eye tracker 124 and/or the head tracker 126 and the processor 106. Moreover, the same or similar signal sampling and processing circuitry 116 that is used with the EEG cap 114 may additionally be used to supply appropriate EOG signals to the processor 106. It will be appreciated that, at least in some embodiments, the system 100 may be implemented without one or all of the user state monitors 112. No matter which, if any, of the user state monitors 112 that are included in the system 100, each supplies appropriate user state data to the processor 106.

The processor 106 is in operable communication with the display device 102, the neurophysiological data collector 104, the user interface 108, and the image database 110 via, for example, one or more communication buses or cables 136. The processor 106 is coupled to receive neurophysiological data from the neurophysiological data collector 104. As noted above, the processor 106 may additionally receive physical response data from the user interface 108. As will be described in more detail further below, the processor 106, based at least in part on one or more of these data, assigns probabilities to discrete sections of an image. The assigned probabilities are representative of the likelihood that the discrete sections of the image include a target entity.

It was additionally noted above that the processor 106, at least in some embodiments, may also receive user state data from the one or more user state monitors 112. In such embodiments, the processor 106 appropriately processes the user data and the neurophysiological data to determine whether one or more of these data, either alone or in combination, indicate the user 101 is in a state that could adversely compromise the effectiveness of the image triage processing, which is described in more detail further below. It is noted that, based on this determination, the processor 106 may generate one or more user alerts and/or vary the pace of one or more portions of the below-described image triage processing.

The processor 106 may include one or more microprocessors, each of which may be any one of numerous known general-purpose microprocessors or application specific processors that operate in response to program instructions. In the depicted embodiment, the processor 106 includes on-board RAM (random access memory) 105, and on-board ROM (read only memory) 107. The program instructions that control the processor 106 may be stored in either or both the RAM 105 and the ROM 107. For example, the operating system software may be stored in the ROM 107, whereas various operating mode software routines and various operational parameters may be stored in the RAM 105. It will be appreciated that this is merely exemplary of one scheme for storing operating system software and software routines, and that various other storage schemes may be implemented. It will also be appreciated that the processor 106 may be implemented using various other circuits, not just one or more programmable processors. For example, digital logic circuits and analog signal processing circuits could also be used.

The image database 110 preferably has various types of imagery collections stored therein. The imagery collection types may vary, and may include, for example, various types of static imagery and various types of video imagery. It will additionally be appreciated that, although the image database 110 is, for clarity and convenience, shown as being stored separate from the processor 106, all or portions of this database 110 could be loaded into the on-board RAM 105, or integrally formed as part of the processor 106, and/or RAM 105, and/or ROM 107. The image database 110, or the image data forming portions thereof, could also be part of one or more non-illustrated devices or systems that are physically separate from the depicted system 100.

As was previously noted, the processor 106 receives neurophysiological data, physical response data, or both, and may additionally receive user state data. The processor 106, based at least in part on one or more of these data, assigns probabilities to discrete sections of an image. These assigned probabilities are representative of the likelihood that these discrete sections of the image include a target entity. The overall process 200 by which the processor 106 implements these outcomes is depicted in flowchart form in FIG. 2, and with reference thereto will now be described in more detail. Before doing so, however, it is noted that the depicted process 200 is merely exemplary of any one of numerous ways of depicting and implementing the overall process to be described. Moreover, before the process 200 is initiated, it is noted that, if neurophysiological data are collected, at least the neurophysiological data collector 104 has preferably been properly applied to the user 101, and appropriately configured to collect neurophysiological data. If included, the one or more user monitors 112 have also preferably been applied to the user 101, and appropriately configured to collect user state data. With this background in mind, it is additionally noted that the numerical parenthetical references in the following description refer to like steps in the flowchart depicted in FIG. 2.

Figure 3:
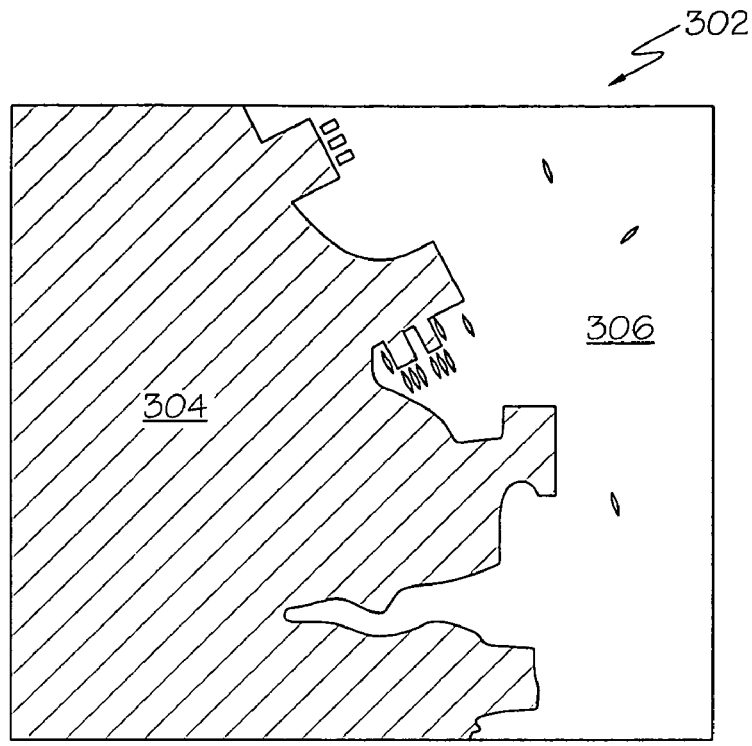
FIG. 3 depicts an exemplary broad area image that may be displayed using the system of FIG. 1.

Turning now to the description of the process 200, it is seen that the processor 106 first retrieves an image from the image database 110 (202). The processor 106 may then command the display device 102 to display the retrieved image to the user 101 in a display region of the display device 102 (204). It will be appreciated that the processor 106 may, in some embodiments, not command the display device 102 to display the image upon its initial retrieval. It will additionally be appreciated that the size of the display region in which the retrieved image and/or the various sub-images that are described further below may also vary. The display region size may depend, for example, on the size and scale of the retrieved image and/or sub-images. Whether or not the retrieved image is initially displayed, in many instances the image may be a broad area image. For example, the image may be a broad area satellite image that depicts a relatively large land area, a relatively large water (e.g., sea or ocean) area, or a relatively large area includes both land and water areas. An exemplary broad area image 302 that may be retrieved from the image database 110 is depicted in FIG. 3. In the depicted example, the displayed broad area image 302 includes both land area 304 and water area 306.

Figure 4:
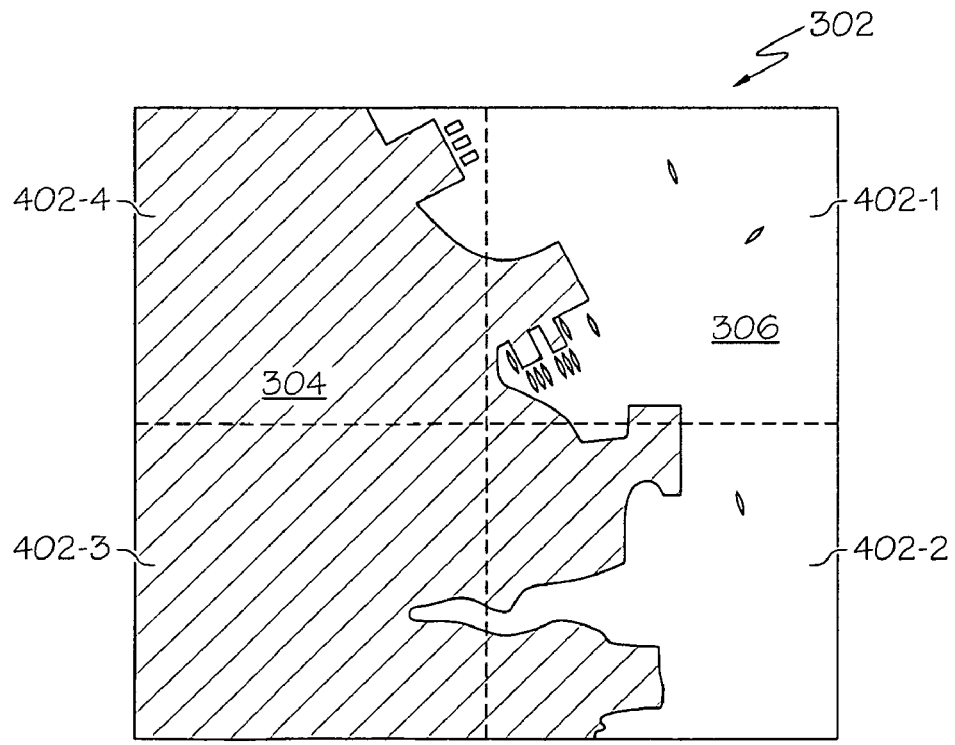
FIG. 4 depicts the exemplary broad area image of FIG. 3 divided into a plurality of sub-images.

Rather than dividing the retrieved broad area image 302 into a plurality of image chips, and then displaying these image chips to the user, the system 100 is configured to recursively divide the retrieved image 302 into a plurality of sub-images (206) and to display the sub-images to the user 101 (208). Specifically, as FIG. 4 depicts, the processor 106 is configured to divide the retrieved image 302 into a plurality sub-images 402 (e.g., 402-1, 402-2, 402-3, . . . 402-N). Preferably, the processor 106 divides the retrieved image 302 into a plurality of equal sized sub-images 402. For example, in the depicted embodiment the processor 106 divides the retrieved image into quadrants, thereby producing four equally sized sub-images 402-1, 402-2, 402-3, 402-4. It will be appreciated that the processor 106 could divide the retrieved image 302 into unequal sized sub-images 402, and that the number of sub-images could be more or less than four.

Returning once again to FIG. 2, after the retrieved image 302 is divided, the processor 106, either automatically or in response to user input signals supplied from the user interface 108, commands the display device 102 to display each sub-image 402 (208). Preferably, the sub-images 402 are presented using a rapid serial visualization presentation (RSVP) technique. Thus, each sub-image 402 is individually displayed, preferably at the same location on the display device 102, in the same display region (i.e., scaled to the same display area as the broad area image 302), for a presentation time period, preferably in a predetermined sequence, and preferably at substantially equivalent luminance levels. The presentation time period of each of these initial sub-images 402 is preferably equal, but may also vary and may, at least in some embodiments, be selected by the user 101.

While the sub-images 402 are being displayed to the user 101, data such as, neurophysiological data, physical response data, or both, are collected from the user 101 (210). In some embodiments, as was previously noted, user state data may additionally be collected via the user interface 108 and the one or more state monitors 112. As was also previously noted, if neurophysiological data are collected, these data are preferably EEG data collected via the multi-channel EEG cap 114. It will be appreciated that, if collected, either the CCD 118 or the keyboard 122 may be used to collect the physical response data. In particular, the user 101 will hit either a predetermined button on the CCD 118 or a predetermined key on the keyboard 122 each time the user 101 believes a displayed sub-image 402 includes a target entity, or at least a portion of a target entity. It will be appreciated that the retrieved image 302 may include any number of target entities.

During neurophysiological data collection, the processor 106, as previously noted, supplies image triggers, or brief pulses, to the neurophysiological data collector 104. The image triggers are supplied each time a sub-image 402 is displayed. During subsequent processing, which is described further below, a segment of neurophysiological data and a segment physical response data are extracted around each image trigger. These segments, referred to as epochs, contain neurophysiological data and physical response data from a predetermined time before an image trigger to a predetermined time after the image trigger. It will be appreciated that the predetermined time period before and after each image trigger, and concomitantly the total length of each epoch of data, may vary.

After the neurophysiological data are collected and, in some embodiments, the physical response data and/or the user state data are collected, a probability is assigned to each sub-image 402 (212). The probability that is assigned to each sub-image 402 is based on these collected data, either alone or in combination, and is representative of the likelihood that the sub-image 402 includes a target entity. It is noted that in a particular preferred embodiment, an epoch of neurophysiological data and an epoch of physical response data associated with each sub-image 402 are supplied to one or more non-illustrated classifiers. The outputs of the classifiers are used to determine the probability to be assigned to each sub-image 402.

Figure 5:
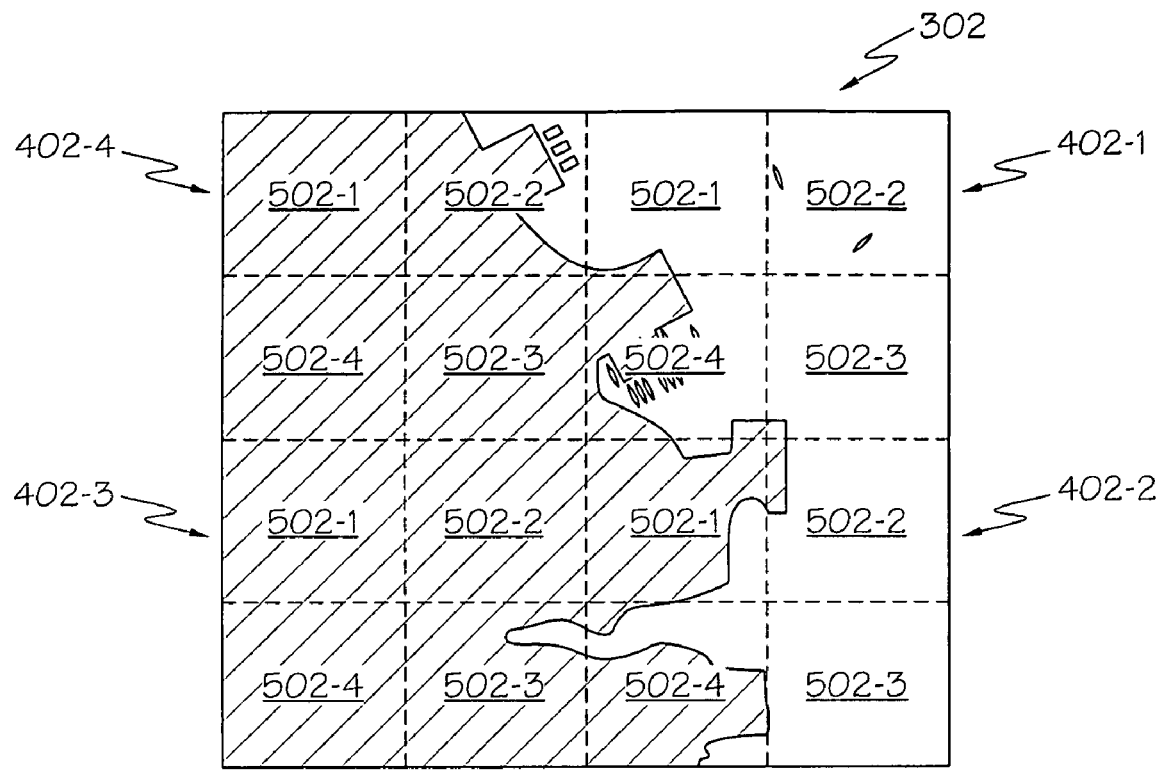
FIG. 5 depicts each sub-image of FIG. 4 further divided into sub-images.

After the data are collected and the probabilities are assigned to each sub-image 402, the processor 106 divides each of the sub-images 402 into another plurality of sub-images. More specifically, and with reference now to FIG. 5, it is seen that each of the initial sub-images 402 depicted in FIG. 4 is further divided into a plurality of sub-images 502 (e.g., 502-1, 502-2, 502-3, . . . 502-N). As was done initially, the processor 106 preferably divides each of the initial sub-images 402 into a plurality of equal sized sub-images 502. For example, in the depicted embodiment the processor 106 again divides each initial sub-image 402 into quadrants, thereby producing four equally sized sub-images 502-1, 502-2, 502-3, 502-4 from each of the initial sub-images 402. It will be appreciated that the processor 106 could divide the initial sub-images 402 into unequal sized sub-images 502, and that the number of sub-images 502 into which each sub-image 402 is divided could be more or less than four.

Returning once again to FIG. 2, after each initial sub-image 402 is divided into the plurality of sub-images 502, the processor 106, either automatically or in response to user input signals supplied from the user interface 108, once again commands the display device 102 to display each sub-image 502 (208), and once again user data are collected (210). Again, the sub-images 502 are preferably presented using the RSVP technique, and each sub-image 502 is individually displayed, preferably at the same location on the display device 102, in the same display region (i.e., scaled to the same display area as the broad area image 302), for a presentation time period, preferably in a predetermined sequence, and preferably at substantially equivalent luminance levels. The presentation time period of each of these subsequent sub-images 502 may be equal. However, in a preferred embodiment the presentation time period varies, based at least in part on the probability assigned to the initial sub-image 402 from whence the sub-image 502 is derived. It will additionally be appreciated that the sequence in which the sub-images 502 are displayed to the user 101 is preferably, though not necessarily, determined based at least in part on the probability assigned to the initial sub-image 402 from whence the sub-image 502 is derived. The variation in presentation time period and image display sequence increases the probability that the user 101 will detect target entities in regions of the image 302 where target entities are most likely to be located.

Figure 2:
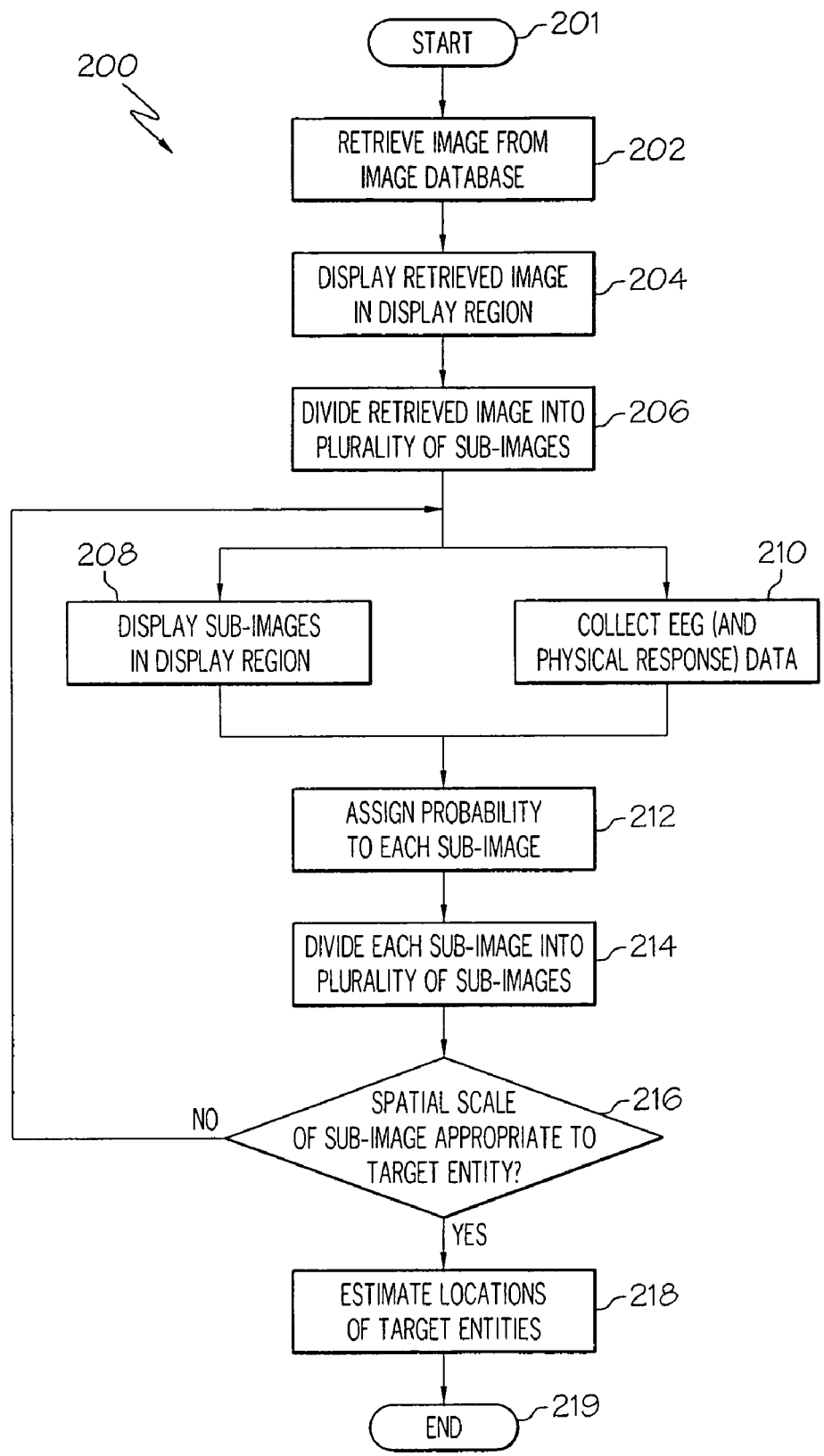
FIG. 2 depicts an exemplary process, in flowchart form, that may be implemented by the image triaging system of FIG. 1.
Figure 6:
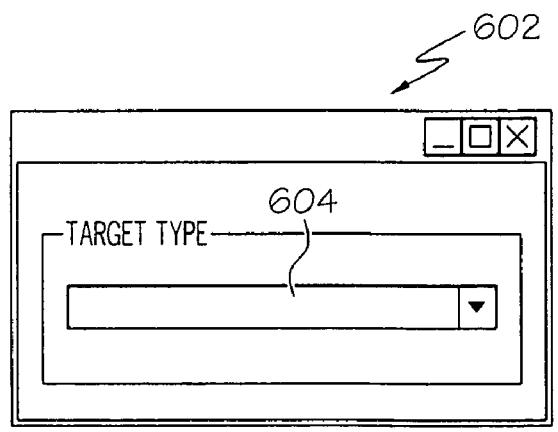
FIG. 6 depicts an exemplary dialog box that may be displayed by the system of FIG. 1.

As FIG. 2 depicts, the above process of further dividing sub-images into smaller sub-images (214), displaying the smaller sub-images (208), collecting data (210), and assigning probabilities to the sub-images (212), is repeated a determined number of times. The number of times that this particular process (214, 208, 210, 212) is repeated may vary. Preferably, however, it is repeated until the spatial scale of each sub-image is appropriate to the searched-for target entity (216). In this regard, it will be appreciated that the system 100 may be configured to allow the user 101 to specify a particular target entity. In such an embodiment, the processor 106 may additionally be configured to command the display device 102, either automatically or in response to other user input signals supplied from the user interface 108, to display an appropriate dialog box. An exemplary embodiment of one such dialog box is depicted in FIG. 6, and allows the user to specify a target entity to be searched for in the retrieved image 302. Although this may be implemented using any one of numerous techniques, in the depicted embodiment the dialog box 602 includes a drop down target entity field 604 that, when selected using the user interface 108, displays a list of various predetermined target entity types from which a target entity type may be selected. It will be appreciated that in other embodiments, this field 604 may be blank, and the user may enter a target entity type via, for example, the user interface 108 (e.g., keyboard 122). It will additionally be appreciated that the specified target entity may vary. Some non-limiting examples include various types of land vehicles, seagoing vessels, special use land masses, weapons sites, or military bases, just to name a few examples.

No matter the specific manner in which the determination is made as to the number of times that the process (214, 208, 210, 212) is repeated, after the process (214, 208, 210, 212) has been repeated the determined number of times, the locations of target entities in the retrieved image 302 are estimated (218). It will be appreciated that the target entity location estimations may be made using any one of numerous techniques. However, in a preferred embodiment the probabilities collected during each recursion of the process (214, 208, 210, 212), which are basically probabilities collected across spatial scales, are integrated and used to estimate target entity locations. These target location estimations may, if desired, be displayed on the retrieved image 302.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A system for conducting image triage of an image that may include one or more target entities, comprising:
    a display device operable to receive display commands and, in response thereto, to display an image in a display region;
    a user interface configured to receive input from a user, the user interface responsive to the input from the user to at least supply user interface signals representative of a target entity to be searched for in an image, and
    a processor coupled to the display device and the user interface, and configured to:
        a) selectively retrieve the image,
        b) divide the retrieved image into a plurality of sub-images,
        c) command the display device to display each sub-image in the display region to a user,
        d) determine the target entity to be searched for,
        e) divide each sub-image that was just displayed into a plurality of sub-images,
        f) command the display device to display each sub-image that was just divided to the user in the display region, and
        g) repeat steps e) and f) a determined number of times, the determined number of times based on the determined target entity.

2. The system of claim 1, further comprising:
    a data collector coupled to the processor and configured to at least selectively collect data from the user at least while each sub-image is being displayed, wherein the processor is further configured to assign a probability to each displayed sub-image, based at least in part on the collected data, that the displayed sub-image at least includes a target entity.

3. The system of claim 2, wherein the processor is further configured to:
   integrate the assigned probabilities after d) and e) have been repeated the determined number of times; and
   estimate locations of the target entities in the retrieved image based on the integrated assigned probabilities.

4. The system of claim 2, wherein the processor is further configured to sort each displayed sub-image into a predetermined display order based on the assigned probability.

5. The system of claim 4, wherein the processor is further configured, during e), to command the display device to display each sub-image in the predetermined display order.

6. The system of claim 2, wherein the processor is further configured to command the display device, during c) and e), to display each sub-image for a presentation time period.

7. The system of claim 6, wherein the processor is further configured to determine the presentation time period for each sub-image based on the assigned probability.

8. The system of claim 2, wherein the processor is further configured to command the data collector to collect the data from the user from a predetermined time period before a sub-image is displayed to a predetermined time period after the sub-image is displayed.

9. The system of claim 8, wherein the collected data are neurophysiological data, physical response data, or both.

10. A system for conducting image triage of an image that may include one or more target entities, comprising:
   a display device operable to receive display commands and, in response thereto, to display an image in a display region; and
   a processor coupled to the display device, the processor configured to receive data representative of a target entity to be searched for in an image, and further configured to:
   a) selectively retrieve the image,
   b) divide the retrieved image into a plurality of sub-images,
   c) command the display device to display each sub-image in the display region to a user,
   d) determine the target entity to be searched for,
   e) divide each sub-image that was just displayed into a plurality of sub-images,
   f) command the display device to display each sub-image that was just divided to the user in the display region, and
   g) repeat steps e) and f) a determined number of times, the determined number of times based on the determined target entity.

* * * * *